United States Patent [19]
Patton

[11] Patent Number: 5,915,277
[45] Date of Patent: Jun. 22, 1999

[54] PROBE AND METHOD FOR INSPECTING AN OBJECT

[75] Inventor: Thadd Clark Patton, Clifton Park, N.Y.

[73] Assignee: General Electric Co., Schenectady, N.Y.

[21] Appl. No.: 08/880,322

[22] Filed: Jun. 23, 1997

[51] Int. Cl.[6] .................................. G01N 9/24
[52] U.S. Cl. ............................................ 73/601
[58] Field of Search ....................... 73/601, 620, 623, 73/627, 629, 643; 324/228

[56] References Cited

U.S. PATENT DOCUMENTS

| | | | |
|---|---|---|---|
| 4,167,878 | 9/1979 | Bottcher et al. | 73/601 |
| 4,217,516 | 8/1980 | Iinuma et al. | 310/335 |
| 4,497,209 | 2/1985 | Kwun et al. | 73/601 |
| 4,678,915 | 7/1987 | Dalquist et al. | 250/358.1 |
| 4,701,659 | 10/1987 | Fujii et al. . | |
| 4,745,809 | 5/1988 | Collins et al. | 73/661 |
| 4,856,337 | 8/1989 | Metala et al. | 73/601 |
| 4,955,235 | 9/1990 | Metala et al. | 73/601 |
| 5,006,801 | 4/1991 | Young | 324/238 |
| 5,025,215 | 6/1991 | Pirl . | |
| 5,047,719 | 9/1991 | Johnson et al. . | |
| 5,062,298 | 11/1991 | Falcoff et al. | 73/597 |
| 5,101,366 | 3/1992 | Cueman et al. | 364/550 |
| 5,161,413 | 11/1992 | Junker et al. | 73/634 |
| 5,182,513 | 1/1993 | Young et al. | 324/232 |
| 5,278,498 | 1/1994 | Vernon et al. . | |
| 5,315,234 | 5/1994 | Sutton, Jr. et al. | 324/242 |

FOREIGN PATENT DOCUMENTS

| | | |
|---|---|---|
| 0301906 | 7/1988 | European Pat. Off. . |
| 0512796 | 5/1992 | European Pat. Off. . |
| 9413411 | 6/1994 | WIPO . |

OTHER PUBLICATIONS

The Modelling and Experimental Study of the Piezofilm Transducer Waveforms in Cylindrical Geometry by Z. Zhang, et al, Review of Progress in Quantitative Nondestructive Evaluation, vol. 11, 1992, pp. 1075–1082.

"NDE of Cylindrically Symmetric Components with Piezofilm Transducers" by David Hsu, et al, Review of Progress in Quantitative Nondestructive Evaluation, vol. 11, 1992, pp. 1083–1090.

*Primary Examiner*—Hezron Williams
*Assistant Examiner*—Thuy Vinh Tran
*Attorney, Agent, or Firm*—David C. Goldman; Marvin Snyder

[57] ABSTRACT

The present invention discloses a probe and method for inspecting a complex shaped object having an irregular surface. In this invention, a flexible film of piezoelectric elements is combined with a flexible film of eddy current elements into a single probe. The probe simultaneously inspects the volume and the surface of the object by using the flexible ultrasonic transducer and the flexible eddy current sensor, respectively.

8 Claims, 2 Drawing Sheets

PROBE AND METHOD FOR INSPECTING AN OBJECT

FIELD OF THE INVENTION

The present invention relates generally to nondestructive testing and more particularly to a probe that incorporates an ultrasonic transducer and an eddy current sensor into a single flexible unit and a method for an inspecting an object with the probe.

BACKGROUND OF THE INVENTION

Nondestructive testing is often used to characterize and detect defects in engineering materials. Two of the most common techniques used in nondestructive testing are ultrasonic inspection and eddy current inspection. Ultrasonic inspection is most commonly used for inspecting the volume of an engineering material, while eddy current inspection is predominately used for inspecting the surface of the material. Typically, in pulse-echo ultrasonic inspection, an ultrasonic transducer is moved over the surface of the engineering material and sends an ultrasound beam of energy inwards towards the material. The ultrasonic transducer receives an ultrasound beam of energy reflecting from the interior of the material. The reflected ultrasound beam of energy contain signals from the volume of the material that are represented by a discrete set of points. The discrete set of points are used to reconstruct a volumetric image of the material. The volumetric image will show defects present within the material. Typically, in driver-pickup eddy current inspection, an eddy current probe uses a drive coil to induce eddy currents within the material and a sense coil to sense secondary magnetic fields that result from the eddy currents. Signals from the secondary magnetic fields are used to generate an image showing discontinuities or flaws in the surface of the material.

Generally, ultrasonic inspection and eddy current inspection are performed independent of each other using systems dedicated to one approach or the other. Inspection of an engineering material using independent ultrasonic and eddy current systems is common because defects cannot be efficiently detected throughout the material using each method alone. For example, if a surface defect is detected by an eddy current probe and the extent of the defect within the material must be determined, then the eddy current probe must be removed and an ultrasonic transducer placed on the location that the defect was detected. Removing the eddy current probe from the material and replacing it with the ultrasonic transducer is time consuming and cumbersome. In order to overcome this problem, some nondestructive inspection systems have combined the ultrasonic transducer and the eddy current into one single unit. However, a problem with this approach is that these systems are unwieldy and unable to conform to complex shaped objects having irregular surfaces, which results in a less than thorough examination. Another problem with the combined ultrasonic and eddy current probe is that combined unit is packaged into larger and often times bulky configurations that cannot be used in tight inspection locations where separate ultrasonic and eddy current probes could be used alone. Yet another problem with the combined ultrasonic and eddy current probe is that the combined unit is packaged into rigid configurations that do not readily allow for inspection of complex curving geometries. Accordingly, there is a need for a flexible nondestructive inspection device that combines an ultrasonic transducer with an eddy current probe in a single unit, in order to inspect complex shaped objects having irregular surfaces.

SUMMARY OF THE INVENTION

This invention is able to inspect complex shaped objects having irregular surfaces by providing a probe that combines flexible piezoelectric film elements used for generating and receiving ultrasonic energies with flexible eddy current drive and sense elements used for inducing and sensing electromagnetic interactions into a single unit. The flexibility of the probe makes it well suited for inspecting objects having smoothly varying concave surfaces, smoothly varying convex surfaces, closed surfaces, internal comers, and external corners. In addition to inspecting complex shaped objects having irregular surfaces, this invention is able to detect and characterize volumetric and surface material properties of these objects without having to endure the redundant inspection efforts associated with using separate and distinct ultrasonic and eddy current inspection systems.

In accordance with this invention, there is provided a probe and method for inspecting an object. In this invention, a flexible ultrasonic transducer and a flexible eddy current sensor are provided. The flexible ultrasonic transducer and the flexible eddy current sensor are coupled together to form the probe. The probe simultaneously inspects the volume and the surface of the object, wherein the flexible ultrasonic transducer inspects the volume of the object and the flexible eddy current sensor inspects the surface of the object.

DETAILED DESCRIPTION OF THE INVENTION

Figure 1:
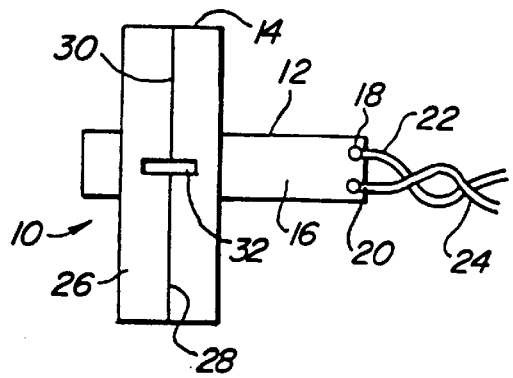
FIG. 1 is a bottom planar view of one embodiment of a probe according to this invention.

FIG. 1 shows a bottom planar view of one embodiment of a probe 10 used to inspect an object. The probe 10 comprises a flexible ultrasonic transducer 12 and a flexible eddy current sensor 14 coupled together to form a single unit. The flexible ultrasonic transducer comprises a flexible film of piezoelectric elements 16. Attached to the flexible film of piezoelectric elements are two eyelets 18 and 20. Wires 22 and 24 are attached to the two eyelets 18 and 20, respectively, through rivets, paste solder, or similar flexible substrate to wire connection methods. The flexible film of piezoelectric elements 16 with eyelets 18 and 20 and wires 22 and 24 is a commercially available piezo film sensor provided by AMP®. Other types of flexible film of piezoelectric elements may be used with this invention; such as the polyvinylidine fluoride (PVDF) films provided by Ktech Corporation. The flexible eddy current sensor 14 comprises a flexible film of eddy current drive and sense elements 26 and 32. The flexible film of eddy current elements is a multi-layer polyimide film matrix such as KAPTON having flexible electric leads 28 and 30. Although the illustrative embodiment shows a single driving and sensing coil, it is within the scope of this invention to use multiple driving and sensing coil elements. The number, size, shape, orientation, and position of the eddy current elements and the piezoelectric elements is not limited to the implementation shown in FIG. 1 and can vary.

Figure 2:
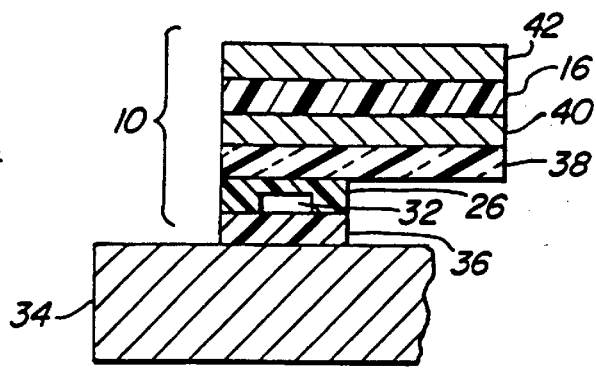
FIG. 2 is a cross sectional side elevational view of the probe shown in FIG. 1 with a surface and volume of an object to be tested.

FIG. 2 shows a cross sectional side elevational view of the probe 10 shown in FIG. 1 with a surface and volume of an object 34 to be tested. The surface of the object is shown to be smooth for ease of illustrating this invention, however the probe is particularly well suited for inspecting complex shaped objects having irregular surfaces such as formed sheet metal, thin-walled metallic tubing, and forged shapes with parallel front and back surfaces. These complex shaped geometries have smoothly varying concave surfaces, smoothly varying convex surfaces, closed surfaces, internal corners, and external corners. The flexibility of the probe 10 makes it well suited for inspecting objects having these types of surfaces. Referring back to FIG. 2, the probe 10 is shown with a protective cover 36 overlying the surface of the object 34. The protective cover can be a polyimide mesh fabric, TEFLON tape or other inert material that contacts the surface of the object 34 being tested and is used to lessen the wear and tear associated with scanning objects with the probe 10. The polyimide film matrix 15 is placed over the protective cover 36. The eddy current driving coil 26 and sensing coil 32 are disposed in the polyimide film 15. The ultrasonic transducer 12 may also be imbedded into the polyimide film 15 through the fabrication process used to generate the eddy current sensor 14. A transparent adhesive 38 bonds the flexible eddy current sensor 14 to the flexible ultrasonic transducer 12. The transparent adhesive 38 may be a commercially available adhesive like 3M Scotch Brand® double sided adhesive. In the illustrative embodiment, the transparent adhesive 38 bonds the polyimide film 15 to a first electrode 40. The flexible film of piezoelectric elements 16 is disposed over the first electrode 40 and a second electrode 42 is disposed over the flexible film of piezoelectric elements 16.

The flexible film of piezoelectric elements 16 is located behind the flexible film of eddy current elements 26 so that the eddy current elements lie proximal to the surface of the object 34 being inspected, outside the active area of the piezoelectric elements. The arrangement of having the eddy current elements next to the surface ensures that there is a maximized electromagnetic field coupling with the inspected object 34. The film thickness of the eddy current elements has a minimal influence on the generation of the ultrasonic beams of energy produced from the film of piezoelectric elements 16. The only effects that the film of eddy current elements have on the film of piezoelectric elements is reflection impedance and attenuation. The capacitive nature of the film of piezoelectric elements is susceptible to electromagnetic interference, particularly from the film of eddy current elements. However, the electromagnetic interference may be minimized by adding a shielding, placing the eddy current elements outside of the active area of the film of piezoelectric elements, and switching/synchronizing the driving currents between the piezoelectric elements and the eddy current elements so that they are not activated simultaneously.

Figure 3:
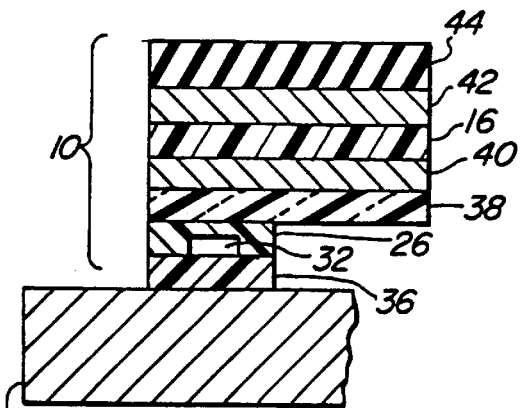
FIG. 3. is a cross sectional side elevational view of the probe shown in FIG. 2 with a backing material.

FIG. 3 is a cross sectional side elevational view of the probe shown in FIG. 2 with a backing material 44. The backing material 44 is used to provide a constant coupling force to and from the object under inspection. In addition, to providing a constant coupling force, the backing material directs the ultrasonic beams of energy towards the object and provides high attenuation for diminishing any reverberations. In the illustrative embodiment, the backing material 44 is a rubber material, however other backing material having a lossy material such as epoxy resins, RTV, may be used. The specific choice of backing material depends on the particular application of the probe 10 and the desired frequency response of the ultrasonic transducer.

The probe 10 enables an operator to simultaneously inspect the volume and the surface of an object. The probe 10 is used, as with any nondestructive sensor, to inspect an object by first placing the sensors into a fixture or device for mechanized or manual manipulation of the sensors over the object under inspection. The selection of fixturing devices and manipulation depends on the inspection requirements of the object at hand. Next, each sensor is calibrated with respect to a reference object with known physical properties. The calibration procedures are used to guarantee the performance of the sensors and their respective instrumentation settings are sufficient to obtain the appropriate level of inspection resolution. During the calibration process, the same fixturing devices and manipulation methods are used for each sensor calibration procedure. Finally, the sensors and associated fixturing and manipulation schemes are positioned and scanned over the object of inspection to provide a representative volumetric and surface characterization of the object with respect to the reference objects.

Figure 4:
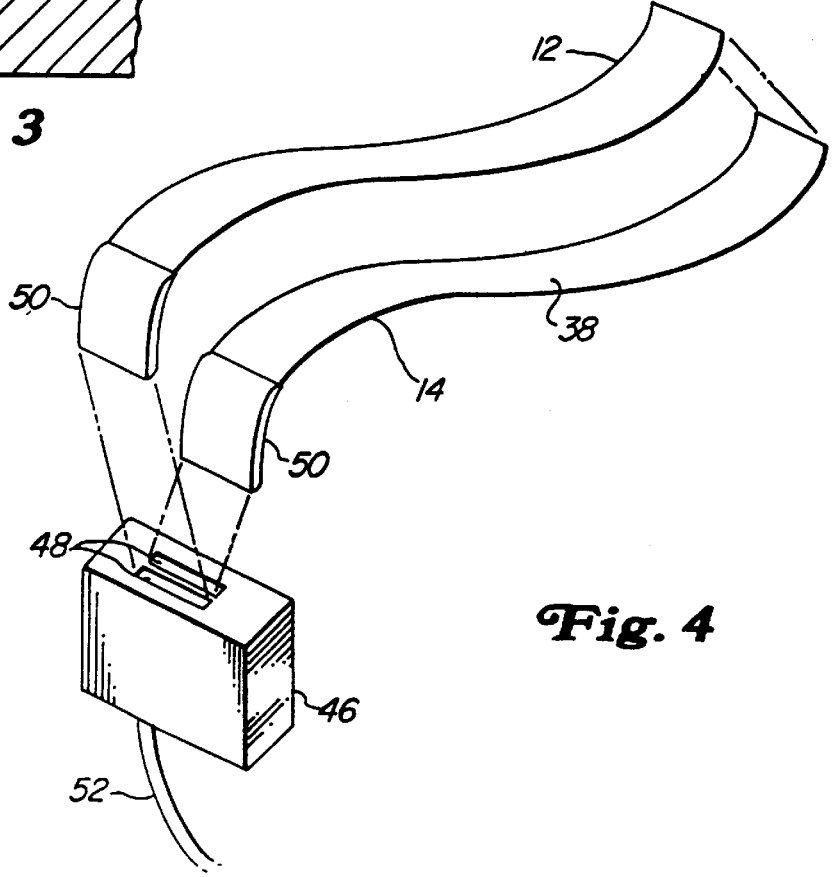
FIG. 4 is a schematic showing the probe connected to electronic circuitry.

FIG. 4 is a schematic showing the probe 10 connected to an electrical connection 46. The electrical connection 46 comprises two slots 48 for receiving the flexible ultrasonic transducer 12 and the flexible eddy current sensor 14. The flexible ultrasonic transducer 12 and the flexible eddy current sensor 14 are coupled to the electrical connection 46 via connectors 50 which are complementary to the slots 48. The electrical connection 46 also comprises an electric wire bundle 52 for providing power and ground to the flexible ultrasonic transducer 12 and the flexible eddy current sensor 14. The electric wire bundle also includes other components such common resistors and transformers.

Figure 5:
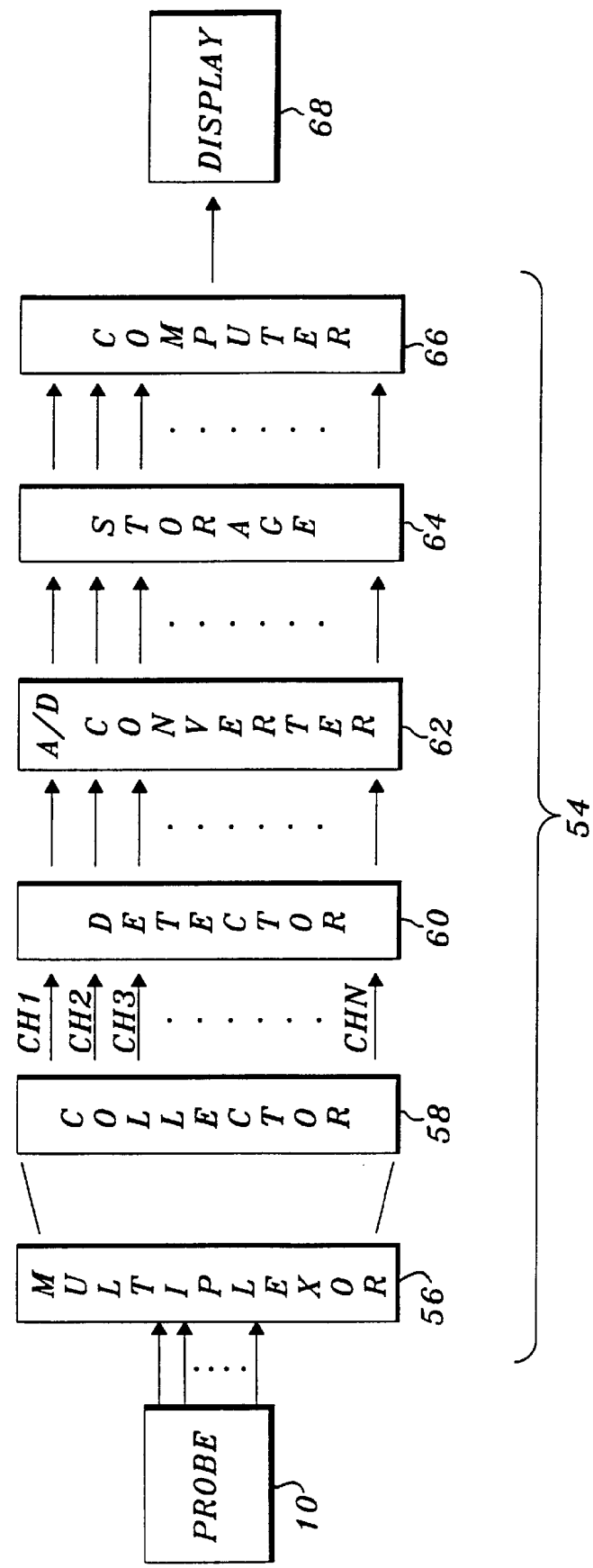
FIG. 5 is schematic showing the probe connected to a multi-channel inspection system.

The probe 10 can be connected to either a multiple or single channel electronic system for processing the data generated from the probe. An example of a multi-channel inspection system 54 coupled to the probe 10 is shown in FIG. 5. Each measurement by the probe 10 is multiplexed by a multiplexor 56 to a collector 58 and separated into independent parallel data channels (CH1, CH2, . . . CHN). Discrete measurement signals are independently collected and inputted to a demodulating synchronous detector 60 to obtain demodulated signals. The signals are formatted for digital processing by an analog to digital converter 62. The digitized signals are then stored in a storage means 64. A computer 66 processes the signals to generate an image of the object showing surface and volume defects of the object. The image is then displayed on a display means 68.

It is therefore apparent that there has been provided in accordance with the present invention, a probe and method for inspecting an object. The invention has been described with reference to several embodiments, however, it will be appreciated that variations and modifications can be effected by a person of ordinary skill in the art without departing from the scope of the invention.

I claim:

1. A probe for inspecting an object, comprising:
   a flexible ultrasonic transducer comprising a flexible film of piezoelectric elements; and
   a flexible eddy current sensor coupled to the flexible ultrasonic transducer comprising a flexible film of eddy current elements, the flexible ultrasonic transducer and the flexible eddy current sensor forming a single unit for simultaneously inspecting the volume and the surface of the object, wherein the flexible film of piezoelectric elements is coupled behind the flexible film of eddy current elements and the flexible film of eddy current elements is proximal to the surface of the object and outside the active area of the flexible film of piezoelectric elements.

2. The probe according to claim 1, further comprising an electrical connection coupled to the flexible ultrasonic transducer and the flexible eddy current sensor.

3. The probe according to claim 1, further comprising a backing material coupled to the flexible ultrasonic transducer and the flexible eddy current sensor.

4. The probe according to claim 1, wherein the object has a complex shaped geometry.

5. A method for inspecting an object, comprising the steps of:

provinding a flexible ultrasonic transducer comprising a flexible film of piezoelectric elements;

providing a flexible eddy current sensor comprising a flexible film of eddy current elements;

coupling the flexible ultrasonic transducer to the flexible eddy current sensor to form a probe, wherein the flexible film of piezoelectric elements is coupled behind the flexible film of eddy current elements;

simultaneously inspecting the volume and the surface of the object with the probe, wherein the flexible ultrasonic transducer inspects the volume of the object and the flexible eddy current sensor inspects the surface of the object, wherein the flexible film of eddy current elements is proximal to the surface of the object and outside the active area of the flexible film of piezoelectric elements.

6. The method according to claim 5, further comprising connecting an electrical connection to the probe.

7. The method according to claim 5, further comprising attaching a backing material to the probe.

8. The method according to claim 5, wherein the object has a complex shaped geometry.

* * * * *